United States Patent [19]

Tan

[11] Patent Number: 5,024,226
[45] Date of Patent: Jun. 18, 1991

[54] EPIDURAL OXYGEN SENSOR

[75] Inventor: Josef K. S. Tan, Tampa, Fla.

[73] Assignee: Critikon, Inc., Tampa, Fla.

[21] Appl. No.: 394,997

[22] Filed: Aug. 17, 1989

[51] Int. Cl.$^5$ ................................................. A61B 5/00
[52] U.S. Cl. ..................................... 128/633; 128/666
[58] Field of Search ................ 128/632, 633, 634, 665, 128/666; 356/40

[56] References Cited

U.S. PATENT DOCUMENTS

| | | | |
|---|---|---|---|
| 4,621,643 | 11/1986 | New Jr. et al. | 128/666 |
| 4,623,789 | 11/1986 | Ikeda et al. | 604/175 |
| 4,714,080 | 12/1987 | Edgar Jr. et al. | 128/666 |
| 4,784,150 | 11/1988 | Voorhies et al. | 128/664 |
| 4,825,872 | 5/1989 | Tun et al. | 128/665 |
| 4,865,038 | 9/1984 | Rich et al. | 128/665 |
| 4,867,557 | 9/1989 | Takatani et al. | 356/41 |
| 4,928,691 | 5/1990 | Nicolson et al. | 128/633 |
| 4,938,218 | 7/1990 | Goodman et al. | 128/633 |

FOREIGN PATENT DOCUMENTS

| | | | |
|---|---|---|---|
| 0094749 | 11/1983 | European Pat. Off. | 128/633 |
| 0135840 | 4/1985 | European Pat. Off. | 128/633 |
| 3152963 | 10/1983 | Fed. Rep. of Germany | 128/633 |

OTHER PUBLICATIONS

"Cerebral Oxidative Metabolism and Blood Flow During Acute Hypoglycemia and Recovery in Unaesthetized Rate", Journ. of Neurochem., 1982 p. 397.

"Regional Acetylcholine Metabolism in Brain During Acute Hypoglycemia and Recovery", Journ. Neurochem., 1985 at p. 94 et seq.

Yee, Sinclair et al., "A Proposed Minature Red/Infrared Oximeter . . .", IEEE Trans, Biomed. Eng. (USA), vol. BME-24 NO. 2 (Mar. 1977).

Primary Examiner—Lee S. Cohen
Assistant Examiner—John D. Zele
Attorney, Agent, or Firm—Paul A. Coletti

[57] ABSTRACT

A sensor for measuring the oxygen availability of blood flow within the skull is described. In a first embodiment the sensor comprises a photodetector and a pair of light emitting diodes surface mounted near the end of a length of flexible printed wiring. The sensor is sealed by a coating of rubber or polymeric material which has an optical window over the photodetector and light emitting diodes. The sensor is inserted through a burr hole drilled in the skull and slides between the skull and the dura of the drain. The light emitting diodes are pulsed to illuminate blood flow in the brain beneath the dura with light, and light reflected by the blood is received by the photodetector and converted to electrical signals. The signals are processed by a pulse oximeter to provide an indication of blood availability. In a second embodiment the photodetector and light emitting diodes are mounted at the end of a core of compressible foam extending from the end of a hollow bone screw. As the bone screw is screwed into a burr hole in the skull the photodetector and light emitting diodes will contact the dura and the foam will compress to maintain optical contact between the electrical components and the dura. Light from the diodes is reflected by blood in the dura and brain, received by the photodetector, and the resultant electrical siganls are processed by the pulse oximeter.

12 Claims, 3 Drawing Sheets

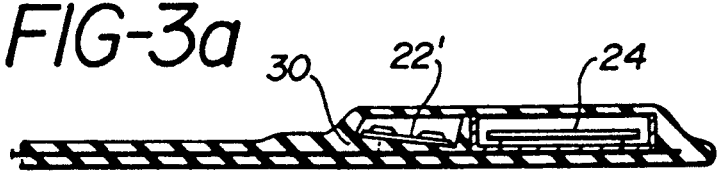
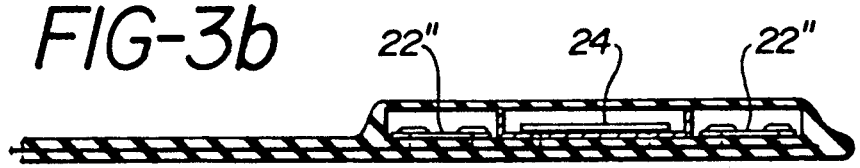
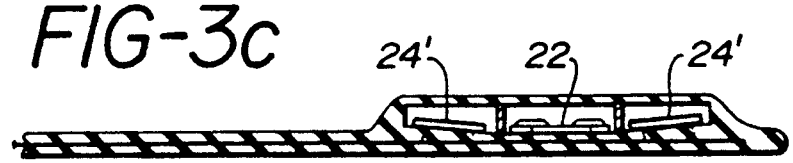
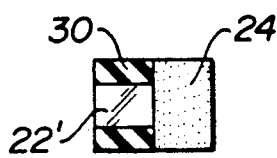 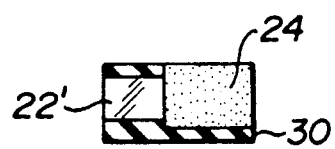 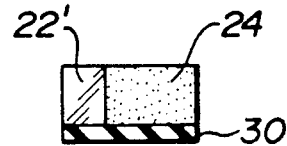
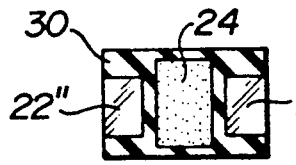 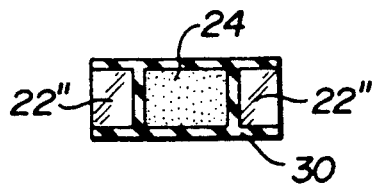 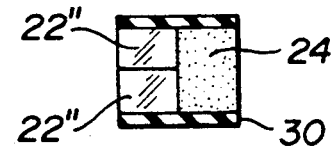
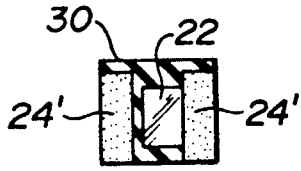 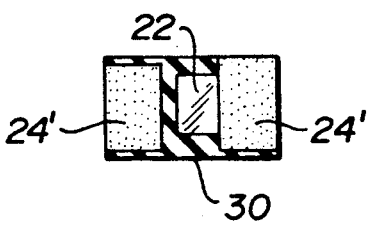 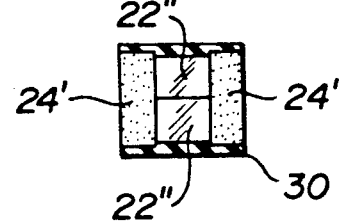

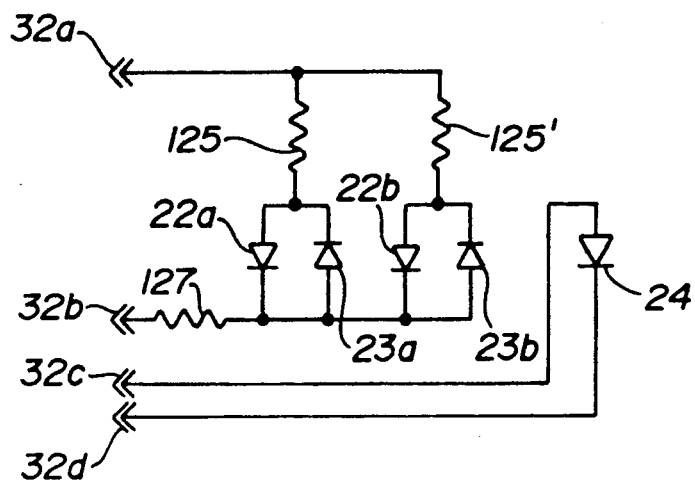
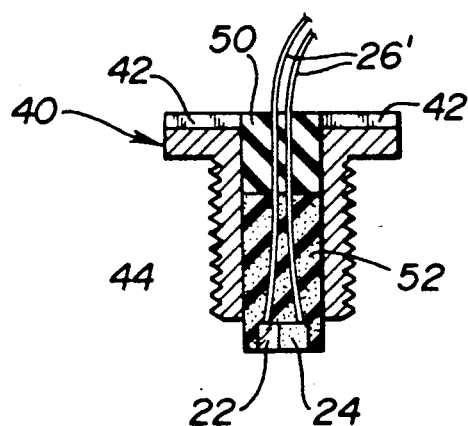
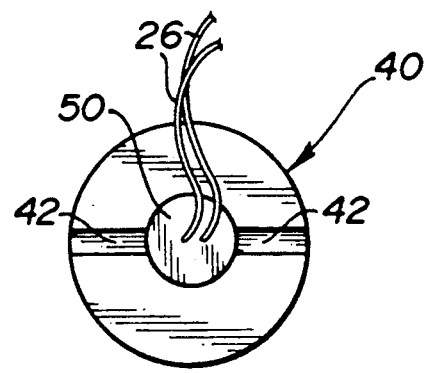
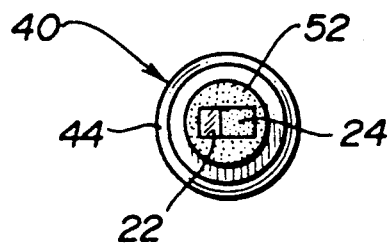

EPIDURAL OXYGEN SENSOR

This invention relates to sensors for determining the oxygen availability of tissues within the skull and, in particular, to such sensor which are placed epidurally through the skull to measure oxygen availability.

During neurological and neurologically related surgical procedures it is oftentimes desirable to continuously monitor the oxygenation of blood which is supplied to the brain. Frequently access is gained to the brain through a borehole in the skull, and a sensor which optically measures oxygenation can then be inserted through such a borehole. An optical sensor should then exhibit numerous design and performance criteria in order to operate satisfactorily in this environment. The sensor must be capable of insertion through the borehole so as to contact tissue where oxygen availability is to be measured The sensor must be soft so that it does not damage neurological tissue, yet be sufficiently rigid in certain dimensions so that it can be maneuvered from outside the skull. It also must be sized to fit inside the borehole and in the location where measurements are to be taken. Furthermore, the sensor must be designed so as to eliminate detection of ambient light which will interfere with detection of the desired optical signals The sensor must also prevent the detection of directly transmitted light from the light source of the sensor.

In accordance with the principles of the present invention, an optical sensor is provided for epidural measurement of blood oxygenation In a first embodiment the sensor comprises a pair of light emitting diodes (LED's) which emit light at two predetermined wavelengths. The sensor also includes a photodetector for receiving light emitted by the LED's which has been reflected from adjacent blood perfused tissue. The LED's and the photodetector are mounted on flexible printed wiring which transmits signals to the LED's and from the photodiode. The components are encapsulated in a soft polymer which is biocompatible. The resultant sensor is thus capable of operation in an epidural environment, and is further capable of being maneuvered into the desired position for epidural measurements.

In a second embodiment the LED's and photodetector are located in a hollow bone screw, with the components opposing the tissue from which measurements are to be taken. The components are backed by a resilient member such as a spring or soft polymeric foam which will compress under gentle pressure within the bone screw to cause the components to contact the dura and maintain optical contact with the dura as it moves with the patient's respiration.

In the drawings:

FIGS. 3a-3c are cross-sectional views of different embodiments of epidural oxygenation sensors of the present invention;

FIGS. 4a-4c, 5a-5c and 6a-6c are plan views of different placements of LED's and photodiodes of epidural oxygenation sensors of the present invention;

FIG. 7 is an electrical schematic of the components of the epidural oxygenation sensor of FIG. 2; and FIGS. 8a-8c are cross-sectional, top, and bottom views of an epidural oxygenation sensor mounted in a hollow bone screw.

Figure 1:
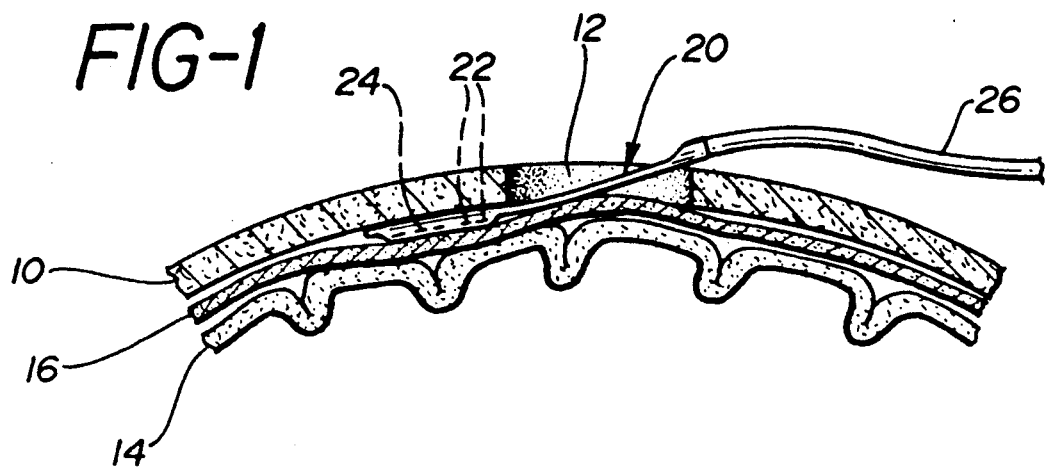
FIG. 1 illustrates a cross-sectional view of the use of an epidural oxygenation sensor constructed in accordance with the present invention.

Referring first to FIG. 1, a skull is shown in which a burr hole 12 has been drilled. Underlying the skull is the dura 16 which encases the brain, and beneath the dura is the cerebrum 14. An epidural oxygenation sensor 20 is inserted through the burr hole 12 for measurement of the oxygenation of blood flowing in the brain. The sensor 20 is inserted through the burr hole and slides between the skull 10 and the dura 16, where it is shielded from ambient light entering the burr hole. At the distal end of the sensor 20 is a photodetector 24 and LED's 22 which face the dura through optical windows in the sensor. The photodetector and LED's are mounted on flexible printed wiring which is connected to a sensor cable 26. The sensor cable is connected to a pulse oximeter (not shown), which provides drive pulses for the LED's, receives electrical signals from the photodetector, and processes the received electrical signals to produce an indication of the oxygen availability of blood in the brain. The sensor is operated in a reflective mode, whereby light of different wavelengths emitted by the LED's is reflected by the blood in the brain and the reflected light is received by the photodetector.

Figure 2:
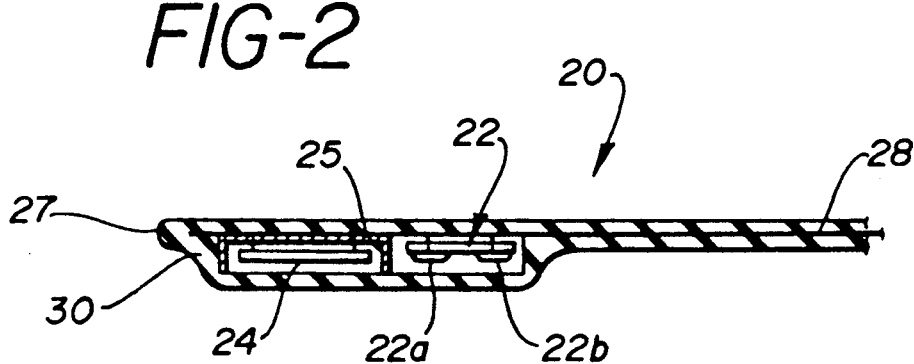
FIG. 2 is a side cross-sectional view of an epidural oxygenation sensor constructed in accordance with the principles of the present invention.

As shown in FIG. 2, the sensor 20 comprises a photodetector 24 and an adjacent pair of LED's 22a and 22b which are surface mounted to leads of flexible printed wiring 28 such as 0.001 inch Kapton TM based printed wiring. The use of surface mounted components and the printed wiring provide a thin sensor which minimizes cerebral compression. Separating the LED's and the photodetector is a light barrier 25 which prevents the direct transmission of light from the LED's to the photodetector. The light barrier may be provided by an opaque epoxy material, but in a preferred embodiment the light barrier is formed of a thin sheet of copper foil. The copper foil not only effectively blocks light from the LED's, but is also connected to a grounded lead of the flexible printed wiring. The copper foil thus shields the photodetector from radio frequency interference such as that emanated during pulsing of the LED's.

The foregoing components are encapsulated by a soft coating 30 of silicone rubber or polyurethane material. The soft coating smoothly rounds the corners and edges of the sensor which prevents injury to the dura by the sensor. The coating also seals the components from moisture and other environmental factors. The coating 30 is optically transmissive to light at the wavelengths of the LED's where it overlies the lower surfaces of the photodetector and the LED's from which light is transmitted and received by these components.

Figure 2A:
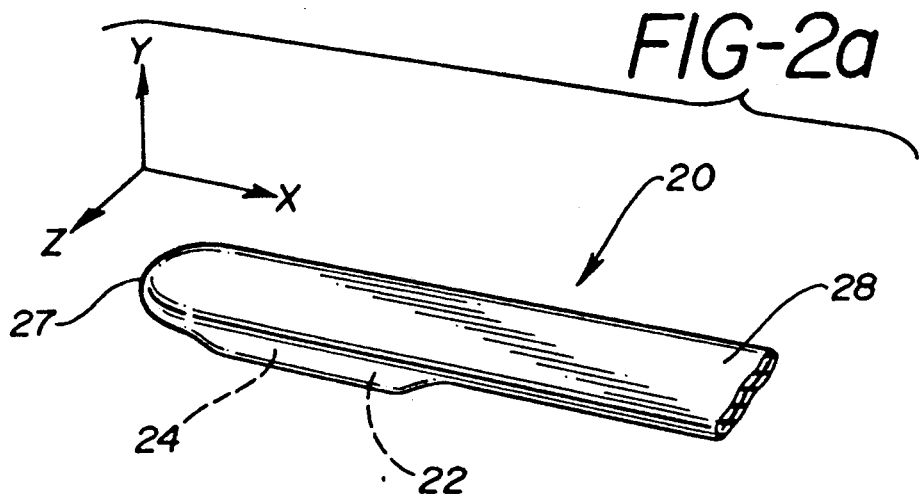
FIG. 2a is a perspective view of an epidural oxygenation sensor constructed in accordance with the principles of the present invention.

FIG. 2a is a perspective view of the sensor 20 of FIG. 2, referenced to x, y, and z axes. As mentioned above, the coating 30 provides the sensor with a smooth, gently rounded profile such as the rounded distal end 27. The sensor is relatively stiff along the portion of the printed wiring where the components are mounted to maintain their relative alignment. In the x dimension the sensor is fairly stiff so that it may be inserted and guided beneath the skull and in contact with the dura. In the z dimension the sensor is stiff to provide maneuverability during placement of the sensor. In the y dimension the sensor proximal the components is flexible to curve through the burr hole and under the skull, which may have a thickness of 2 to 20 mm depending upon the patient.

In order to be capable of sliding between the skull and the dura the sensor should be thin in the y dimension so as not to injure the patient. Preferably the sensor thickness in this dimension should be not greater than 4 mm, and most preferably not greater than 2.5 mm. The sensor should also be not less than about one millimeter in thickness to maintain continuous contact with the dura. This will reduce the occurrence of motion artifacts, as the dura can move as much as ½ mm or more away from the skull during hyperventilation of the patient, for instance.

In the embodiment of FIG. 2 the photodetector 24 is located toward the distal end 27 of the sensor with respect to the LED's 22. This distal placement of the photodetector keeps the photodetector well removed from the burr hole and ambient light passing through the burr hole. FIGS. 3a-3c show other component orientations which may be employed in different sensor embodiments. In FIG. 3a the LED's 22' are canted toward the dura where the dura overlies the photodetector 24, which improves the efficiency of light reflectance. The canted LED's are supported by a filler of the coating material 30. In FIG. 3b two pairs of LED's 22" are located on either side of the phototdetector 24 to illuminate the dura from both sides of the photodetector. In FIG. 3c the pair of LED's 22 is centrally located between a pair of photodetectors 24', the latter being canted toward the area of the dura illuminated above the LED's.

It is desirable for the optical windows of the components which face the dura to be as large as possible so as to maximize optical transmission efficiency. Opposing this desire is the constraint that the sensor must be sized to fit through the burr hole in the skull. To determine the largest components which may fit through a given burr hole diameter, rectangular configurations of components may be calculated which are capable of fitting through the burr hole. FIGS. 4a-6c show component configurations which can fit through a 14 mm diameter burr hole. FIGS. 4a-4c show plan views of component layouts for the single photodetector and pair of LED's employed in the sensors of FIGS. 2 and 3a. In FIG. 4a the LED's 22' and the photodetector are arranged in a layout which measures 8.2 mm by 6.3 mm. In FIG. 4b the rectangular layout measures 10.5 mm by 5.3 mm, and in FIG. 4c the rectangular layout measures 9.3 mm by 5.7 mm. In each layout the coating material 30 is shown in the area outside the boundaries of the electrical components.

FIGS. 5a-5c show component layouts for a 14 mm diameter burr hole using two pairs of LED's 22" and one photodetector 24. In FIG. 5a the rectangular layout measures 10.8 mm by 7.0 mm; in FIG. 5b the layout measures 13.0 mm by 5.5 mm; and in FIG. 5c the layout measures 8.2 mm by 7.3 mm. In a similar manner, FIGS. 6a-6c show component layouts using two photodetectors 24' and one or two pairs of LED's 22 or 22". In FIG. 6a the rectangular layout measures 8.1 mm by 6.8 mm; in FIG. 6b the layout measures 11.5 mm by 6.8 mm; and in FIG. 6c the layout measures 8.6 mm by 7.5 mm.

In FIGS. 4a-6c each LED pair had an area of 3.0 mm by 4.2 mm. The photodetectors in FIGS. 6a and 6c had an area of 2.25 mm by 6.25 mm. In the remaining layouts the photodetectors each had an area of 4.0 mm by 6.25 mm.

FIG. 7 is an electrical schematic of the sensor 20 of FIG. 2. The two LED's 22a and 22b emit light at a red wavelength and are connected in parallel. These two LED's are paralleled by LED's 23a and 23b, which emit light at an infrared wavelength. The LED's are connected in series with respective resistors 25, 25' of values chosen in correspondence with the drive current to be supplied to the LED's. The LED's are also coupled to a biasing resistor 27. The resistors may be mounted in line with the flexible printed wiring, such as the points 32a-32d at which the wiring joins the cable to the pulse oximeter monitor. Points 32c, 32d are connected to leads from photodetector 24. Alternatively the resistors can be functionally incorporated into the printed wiring by proper selection of materials and dimensions.

FIGS. 8a-8c illustrate a further embodiment of an epidural sensor in which the sensor components are located in a hollow bone screw 40. The screw 40 is threaded as indicated at 44 to screw into the skull, and the head of the screw has a slot 42 to turn the screw with an adjustment instrument as more clearly shown in the top plan view of FIG. 8b. A photodetector 24 and a pair of LED's 22 are located at the bottom of a core of soft, compressible foam material 52 in the center of the screw, as shown in the bottom plan view of FIG. 8c. A resilient member 50 is located above the compressible foam 52 in the center of the screw. The resilient member may comprise a metallic spring or a core of silicone rubber or polyurethane. The electrical leads 26' from the LED's and photodetector pass through the foam material 52 and the resilient member 50 and exit through the top of the hollow screw as shown in FIG. 8c.

In use of the sensor embodiment of FIGS. 8a-8c, a hole is drilled in the skull into which the bone screw 40 is screwed. As the bone screw is screwed into the skull, the oximeter monitor is continuously monitored for the onset of oxygen availability readings. When the bottom of the screw with the sensor components contacts the dura, oxygen readings will commence, and will initially occur erratically. As the bone screw is slowly turned the sensor components will make better contact with the dura and the signal quality will improve The contact between the sensor components and the dura is induced in a gentle manner by the compressible foam 52, which will readily compress as the components make contact with the dura to prevent damage to the dura. The resilient member acts to maintain the compression of the foam 52. When consistent readings occur no further turning of the screw is necessary, as the sensor components are in good surface contact with the dura and will gently ride on the dura due to the compressibility of the foam 52.

A preferred technique for using the embodiment of FIGS. 8a-8c is to drill a hole in the skull and screw the bone screw into the hole before locating the sensor in the screw. After the bone screw is in place the sensor with its foam backing material 52 slides into the hollow bone screw, followed by insertion of the resilient member 50. The foam is gently compressed by the resilient member to cause the sensor to make good contact with the dura, a condition which is detected by monitoring the signal quality of the monitor. This technique obviates problems of entangling the sensor wires as the bone screw is screwed into the skull with the sensor already positioned within the bone screw. Only after the bone screw is emplaced is the sensor with its backing and filling materials inserted into the screw, which can then be done without twisting the sensor components and the wiring to the sensor.

This hollow bone screw embodiment is desirable for its ability to completely block ambient light from the sensor components, and by plugging the burr hole with the bone screw infection of the dura is retarded. The sensor can be safely left in place in the burr hole for extended periods of time.

What is claimed is:

1. A sensor for measuring cerebral oxygen availability through a burr hole in the skull by optical reflectance comprising:
    a length of flexible wiring having (a) a distal end and (b) a proximal end which is to be connected to an oximeter;
    a photodetector electrically connected to said flexible wiring in the proximity of said distal end;
    a pair of light emitting diodes connected to said flexible wiring adjacent to said photodetector; and
    a coating encapsulating said photodetector, said light emitting diodes, and said flexible wiring in the proximity of said photodetector and said light emitting diodes, said coating including optical windows where said coating overlies the optical windows of said photodetector and said light emitting diodes which is transmissive to light at the wavelengths of said light emitting diodes, said encapsulated photodetector and said light emitting diodes having a width less than about 20 mm to fit through the diameter of said burr hole and a thickness less than about 4 mm to slide between the skull and dura.

2. The sensor of claim 1, further including a light barrier positioned between said photodetector and said light emitting diodes which shields said photodetector from the direct reception of light from said light emitting diodes.

3. The sensor of claim 2, wherein said light barrier comprises opaque epoxy.

4. The sensor of claim 2, wherein said light barrier comprises metal foil.

5. The sensor of claim 1, wherein said flexible wiring comprises flexible printed wiring.

6. The sensor of claim 1, wherein said coating is silicone rubber.

7. The sensor of claim 1, wherein said coating is polyurethane.

8. The sensor of claim 1, wherein the optical window of said light emitting diodes is canted toward the area above said photodetector.

9. The sensor of claim 1, further comprising a second pair of light emitting diodes located adjacent said photodetector and on the opposite side of said photodetector as said first-named pair of light emitting diodes.

10. The sensor of claim 1, further comprising a second photodetector located adjacent said light emitting diodes on the opposite side of said light emitting diodes as said first-named photodetector.

11. The sensor of claim 10, wherein said photodetectors are canted toward the area above said light emitting diodes.

12. A method of epidurally sensing oxygen availability comprising the steps of:
    drilling a burr hole in a skull;
    inserting a length of flexible wiring connected to a photodetector and a pair of light emitting diodes mounted in the proximity of the distal end of said wiring, said wiring, said photodetector, and said light emitting diodes encapsulated in a coating through said burr hole and between the skull and the dura, said encapsulated photodetector and said light emitting diodes having a width less than about 20 mm to fit through the diameter of said burr hole and a thickness less than about 4 mm to slide between the skull and dura, with the optical windows of said photodetector and said light emitting diodes opposing the dura;
    energizing said light emitting diodes, and receiving electrical signals from said photodetector resulting from the reception of reflected light emanating from said diodes, by way of said flexible wiring; and
    processing said electrical signals to produce an indication of blood oxygen availability.

* * * * *